United States Patent
Bhat et al.

(10) Patent No.: US 9,931,520 B2
(45) Date of Patent: Apr. 3, 2018

(54) DISINFECTION USING LIGHT THERAPY

(71) Applicant: PRS Medical Technologies, Inc., Atherton, CA (US)

(72) Inventors: Nikhil Bhat, Fremont, CA (US); George Y. Choi, Atherton, CA (US); Luiz B. Da Silva, Danville, CA (US)

(73) Assignee: PRS Medical Technologies, Inc., Menlo Park, CA (US)

( * ) Notice: Subject to any disclaimer, the term of this patent is extended or adjusted under 35 U.S.C. 154(b) by 326 days.

(21) Appl. No.: 14/577,955

(22) Filed: Dec. 19, 2014

(65) Prior Publication Data

US 2015/0196776 A1    Jul. 16, 2015

Related U.S. Application Data

(60) Provisional application No. 61/918,530, filed on Dec. 19, 2013.

(51) Int. Cl.
| | |
|---|---|
| *A61N 5/06* | (2006.01) |
| *H05B 3/34* | (2006.01) |
| *A61L 2/04* | (2006.01) |

(52) U.S. Cl.
CPC .............. *A61N 5/0624* (2013.01); *A61L 2/04* (2013.01); *H05B 3/34* (2013.01); *A61L 2202/26* (2013.01); *A61N 2005/063* (2013.01)

(58) Field of Classification Search
CPC ............ A61N 5/0624; A61L 2/04; H05B 3/34
See application file for complete search history.

(56) References Cited

U.S. PATENT DOCUMENTS

| | | | | |
|---|---|---|---|---|
| 6,094,767 | A * | 8/2000 | Iimura | A46B 15/0002 15/105 |
| 6,653,647 | B1 * | 11/2003 | Vilarasau Alegre | A61L 9/20 15/304 |
| 7,459,694 | B2 * | 12/2008 | Scheir | A61L 2/10 250/454.11 |
| 7,703,262 | B2 * | 4/2010 | Till | A61L 2/10 250/455.11 |
| 2005/0201910 | A1 * | 9/2005 | Shou | A61L 2/06 422/292 |
| 2008/0199353 | A1 * | 8/2008 | Mlodzinski | A61J 1/20 422/24 |
| 2010/0319125 | A1 * | 12/2010 | Ko | A47C 21/048 5/423 |
| 2011/0024649 | A1 * | 2/2011 | Merkle | A45C 11/005 250/492.1 |

(Continued)

FOREIGN PATENT DOCUMENTS

KR    20090111632 A  * 10/2009  .............. A61L 2/10

OTHER PUBLICATIONS

English translation of KR 20090111632 A, Oct. 27, 2009.*

*Primary Examiner* — Regina M Yoo
(74) *Attorney, Agent, or Firm* — Levine Bagade Han LLP

(57) ABSTRACT

Disinfection using light therapy is described herein where a support platform which is configured to support a region of a patient's body may integrate or incorporate one or more light elements positioned within, upon, or in proximity to the support platform for exposing the patient's body to the light therapy. Additionally, light sources and/or heating elements may also be incorporated with mattresses and/or covers for disinfection prior to patient use.

20 Claims, 6 Drawing Sheets

(56) References Cited

U.S. PATENT DOCUMENTS

| | | |
|---|---|---|
| 2011/0239372 A1 | 10/2011 | Bhat et al. |
| 2013/0019873 A1 | 1/2013 | Choi et al. |
| 2013/0019881 A1 | 1/2013 | Bhat et al. |
| 2013/0092175 A1 | 4/2013 | Bhat et al. |
| 2013/0112213 A1 | 5/2013 | Bhat et al. |
| 2013/0174855 A1 | 7/2013 | Choi et al. |
| 2013/0174856 A1 | 7/2013 | Choi et al. |
| 2013/0174859 A1 | 7/2013 | Bhat et al. |
| 2013/0180530 A1 | 7/2013 | Choi et al. |
| 2013/0180531 A1 | 7/2013 | Choi et al. |
| 2013/0212900 A1* | 8/2013 | Stewart .................. D06F 59/04 34/275 |
| 2013/0298918 A1 | 11/2013 | Choi et al. |
| 2014/0000648 A1* | 1/2014 | Ingle ........................ A61L 2/07 134/1 |
| 2015/0017061 A1* | 1/2015 | Robison .................. C02F 1/325 422/24 |
| 2015/0217300 A1* | 8/2015 | Cooke ..................... B26F 3/004 241/3 |

\* cited by examiner

DISINFECTION USING LIGHT THERAPY

CROSS-REFERENCE TO RELATED APPLICATIONS

This application claims the benefit of priority to U.S. Pat. App. 61/918,530 filed Dec. 19, 2013, which is incorporated herein by reference in its entirety.

FIELD OF THE INVENTION

The present invention relates to devices and methods for healing of wounds using light energy while supporting a patient body or a portion of the patient body.

BACKGROUND OF THE INVENTION

Light therapy has been used previously to treat ulcers and wounds as well as to disinfect surfaces that come into contact with ulcers and wounds or other parts of a patient's body. Ulcers or wounds on the body take time to heal. Some of the wounds are caused by compounding factors such as blood flow occlusion due to high pressures (pressure ulcers), or diabetes etc. Traditional treatments include, negative pressure therapy, medications etc. The challenge with traditional treatments is that if the source of the problem is not addressed the treatments are less effective. For example in the case of sacral pressure ulcers, if the treatment is not coupled with a lower pressure solution the problem will not be solved.

Aside from the use of light therapy to treat ulcers and wounds, light therapy has also been used to disinfect surfaces that come into contact with the ulcers and wounds. For instance, hospital mattresses are generally covered with a cover. A medical bed mattress cover provides outer protection to a medical bed mattress by preventing blood and body fluids from entering the inside (inner core) of the mattress. Types of mattresses may include alternating pressure (ac-powered) air flotation mattresses, non-powered flotation mattresses, and other mattresses that are part of hospital beds. Medical bed mattress covers may be coated with or contain a substance that kills germs (e.g., viruses or bacteria) or prevents bacterial growth. There are multiple terms used to describe medical bed mattress covers: water-resistant (e.g., keeps liquid away from the material), water-proof (e.g., prevents liquid from entering inside the material), or water-repellent (e.g., keeps liquid away from the material and prevents liquid from entering inside the material).

The FDA typically receives reports associated with medical bed mattress covers failing to prevent blood and body fluids from leaking into the mattress (fluid ingress). Fluid ingress may occur if mattress covers become worn or damaged from small holes or rips in the fabric or from incorrect cleaning, disinfecting and laundering procedures. The zipper on the cover may also allow fluid to penetrate the mattress. Some reports indicate that if blood and body fluids from one patient penetrate a mattress, they can later leak out from the mattress when another patient is placed on the bed. Patients are at risk for infection if they come into contact with blood and body fluids from other patients.

Medical literature shows that damaged and wet (soiled) mattresses can be a source of contamination during infection outbreaks. The FDA is concerned that fluid ingress from worn or damaged medical bed mattress covers may be widespread and largely under-recognized by health care providers, health care facility staff, and caregivers.

In order to decontaminate mattresses, the covers can be removed and the mattresses aerated; however, doing so is labor intensive and time consuming. Alternatively, light can be illuminated in the entire room or directly upon a mattress; however, simple exposure to light may not kill all bacteria and may not reach below the covers to a required depth.

Accordingly, there exists a need for treatment devices and methods which can facilitate the healing of ulcers or wounds without occluding blood flow to the body regions as well as disinfect surfaces that may come into contact with the ulcers or wounds or other body portions.

SUMMARY OF THE INVENTION

Disinfection using light therapy may be used to disinfect a support platform such as a mattress and/or cover which is configured to support a region of a patient's body. The support or mattress and/or cover may integrate or incorporate one or more light elements positioned within, upon, or in proximity to the support platform for exposing the patient's body to the light therapy. Additionally, light sources and/or heating elements may also be incorporated with mattresses and/or covers for disinfection prior to patient use In one method, a light may be illuminated upon a first region of a mattress or cover, wherein the light is tuned to emit one or more wavelengths suitable for disinfecting one or more bacterial strains present upon the mattress or cover. The light may then be moved to at least a second region of the mattress or cover after a predetermined period of time while under control of a controller.

Generally, the device for disinfecting a supporting surface may comprise a light source which is tuned to emit one or more wavelengths suitable for disinfecting one or more bacterial strains present upon a mattress or cover, an actuator for moving the light source from a first region of the mattress or cover to a second region, and a controller in communication with the light source and actuator, wherein the controller is programmed to move the light source after a predetermined period of time.

Additionally, a blanket or cover may be placed over a mattress for disinfecting a surface of the mattress. Such a method may generally comprise positioning the blanket or cover over a mattress or cover such that the blanket or cover is in thermal communication with the mattress or cover, and heating the blanket to a temperature sufficient to disinfect the mattress or cover.

The blanket or cover for disinfecting may generally comprise a blanket or covering configured for positioning at least partially over a mattress or cover, one or more heating elements positioned within or upon the blanket or covering, and a controller in communication with the one or more heating elements, wherein the controller is programmed to heat the one or more heating elements to a temperature sufficient to disinfect the mattress or cover.

Aside from the mattress or cover, a support platform such as a cushioning device may be used with a disinfecting light. Generally, such an apparatus may comprise a first support having a first contact surface for contacting a portion of a body and a second surface opposite to the first surface, the first support defining a central chamber and a peripheral chamber surrounding the central chamber, wherein the first support is filled with a first gas or liquid, a second support attached to the first support along the first contact surface, wherein the second support is filled with a second gas or liquid which is relatively more viscous than the first gas or liquid, and one or more light elements positioned within, upon, or in proximity to the apparatus such that the one or more light elements are in transmissive communication through the chambers and with the first contact surface for exposing the patient's body to light therapy.

A disinfecting light source can be integrated in a number of different configurations with a conformable support assembly configured to conform to particular regions of a patient's body where pressure ulcers tend to form, e.g., sacrum, trochanter, ischium, head, elbow, heel, as well as any other region of the body where support is desired. Such support is particularly desired when the patient sits, lies, or stands for an extended period of time such as sitting in a wheelchair.

In one variation, the multi-layer cushion support may generally comprise a first support having a first contact surface for contacting a portion of a body and a second surface opposite to the first surface, the first support defining a central chamber and a peripheral chamber surrounding the central chamber, wherein the first support is filled with a first gas or liquid and a second support attached to the first support along the first contact surface, wherein the second support is filled with a second gas or liquid which is relatively more viscous than the first gas or liquid. In particular, the first support may be filled with a volume of air and the second support may be filled with oil which is less than the volume of air.

Generally in use, the multi-layer cushion support may be used to support a portion of a patient's body by providing a multi-layer cushion support comprising a first support having a first contact surface and a second surface opposite to the first surface where the first support defines a central chamber and a peripheral chamber surrounding the central chamber, and a second support attached to the first support along the first contact surface, wherein the first support is filled with a first gas or liquid and the second support is filled with a second gas or liquid which is relatively more viscous than the first gas or liquid and positioning the second support adjacent to the portion of the body.

With this multi-layer support, one or more light sources may be integrated or incorporated to transmit light through the support (in particular through the fluid contained within the support) for illumination upon the patient body in contact with the support to facilitate disinfection of the wound or ulcer or upon a covering to disinfect the covering. The multi-layered cushioning support may generally comprise several interconnected chambers configured to have a central support region and a surrounding support region which are in fluid communication with one another. The multi-layered support may be optionally filled with a gas (such as air) or liquid (such as water or mineral oil) or a combination of both. The multi-layered support may also be sized in various dimensions suitable for placement under a patient body, e.g., 18 in.×20 in. for use as a cushion such as on a wheelchair. The multi-layered support may also incorporate a relatively smaller secondary chamber formed by an additional layer attached (such as by welding) upon the surface of the central support region such that the region surrounds this secondary chamber. The secondary chamber may be filled by a volume of liquid, such as mineral oil, which is relatively more viscous than the gas or liquid filled within the central support region or surrounding support region. Moreover, this secondary chamber may remain fluidly disconnected from the central support region and the surrounding support region.

A cushioning foam layer may be positioned adjacent to the support provided that this cushioning foam layer is positioned along a bottom surface of the support, i.e., along a surface of the support opposite from the secondary chamber. This is to allow for the multi-layered support and secondary chamber to come into direct contact against the patient's body without any other materials interfering (aside from the cover). The cushioning foam layer may be comprised of, e.g., different density polyurethane foams, which can be fabricated into different sizes and thicknesses (e.g., 17 in.×19 in.×0.5 in.) depending upon the desired application. The foam layer can be alternatively replaced by other cushioning designs such as a gel-type material, biasing springs, etc.

The cover may envelope both the multi-layer support and the foam layer and may also be fabricated from various materials which can be breathable and waterproof. The surface of the cover may also be made to have, e.g., an anti-skid surface, over its entire surface or along selective surfaces such as the bottom surface in contact with a platform. The cover may be sized (e.g., 18 in.×20 in.×1.5 in.) similarly to the multi-layer support and foam layer which may both be inserted into the cover through an opening defined along one of the edges of the cover. Additionally, while the individual layers may be maintained in their relative positioning by various mechanisms such as straps, fasteners, adhesives, etc., their relative positioning may also be maintained by the cover. Also, while the cover may be placed atop the secondary chamber for direct contact against the patient's body, the cover is sufficiently thin enough so as not to interfere with the cushioning support provided the layers.

The cushioning foam layer is positioned along a bottom surface of the support, i.e., along a surface of the support opposite from the secondary chamber, so that the secondary chamber and multi-layer support may be positioned into direct contact through the cover, if present, against the patient's body. Having the secondary chamber of the support placed into contact against the patient's body allows for effective pressure distribution throughout the support while the foam positioned beneath the support (i.e., along the surface of the support opposite of the secondary chamber and away from the patient's body) provides for further cushioning support of the patient's body.

However, other variations of the cushioning support may include one example where the foam layer may be positioned atop the multi-layer support. In this variation, the foam layer may be positioned along the same surface of the secondary chamber such that the foam layer comes into contact through the cover with the patient's body.

Turning now to the multi-layer support, the secondary chamber may be formed atop the support via attachment along its edges which may be welded, adhered, or otherwise attached. While the secondary chamber may form a single chamber, one or more barriers or boundaries may be formed along the secondary chamber at least partially dividing the secondary chamber into one or more sub-chambers which are fluidly connected to one another. The inclusion of the barriers or boundaries may effectively slow or inhibit the flow of any fluids contained within the secondary chamber from shifting to quickly such as when the patient adjusts their body position upon the support.

Moreover, the secondary chamber may be formed to have an overall volume of, e.g., 0.6 liters, although this volume may be decreased or increased depending upon the desired results and the type of liquid contained within the chamber. This variation may contain, e.g., 0.6 liters of mineral oil, as the oil may help in reducing the pressure in combination with an underlying air layer contained within the remaining chamber of the support. When in use, the oil layer within the chamber may be cradled by the underlying air chamber to prevent any potential "edge effects" associated with fluid interfaces. Moreover, the inclusion of the oil layer within the chamber may also facilitate the delivery of cooling or heating therapy against the patient body as oil may be cooled or heated by any number of passive or active methods.

Variations of the multi-layered support described herein may be used for supporting other regions of the body. For instance, an embodiment for supportive use of the patient's heels may similarly utilize the same features. Such a variation may be designed to have dimensions scaled appropriately for supporting a heel (e.g., 10 to 13 in. width, 28 to 35 in. length, and 2 to 8 in. height) such that the support may be positioned below the calf when the patient is lying upon a bed so that the heel is lifted off the surface of the bed. The heel protector can also be designed to have an incline to give a gentle slope.

Aside from cushioning supports, disinfection of hospital mattresses using light has also been accomplished. Bacteria and other pathogens are typically found below the cover of the hospital mattress and can lead to hospital acquired infections. To prevent this, a mattress or cushion design can include one or more sources of light which can kill bacteria and disinfect the mattress. These sources can be piped inside of the mattress under the cover or upon the exterior of the mattress and/or cover and can be turned on after every patient use to kill any bacteria and disinfect any mattress.

In one variation, a light and/or heat source may be positioned over a mattress and/or cover to disinfect the mattress and/or cover. In another variation, the light disinfecting system can also be designed as a heating/lighting blanket which may be placed over the mattress for disinfection. In yet another variation, the light disinfecting system can be integrated as a fluid-based layer which may be optionally sandwiched between the cover and mattress. In yet another variation, a thermochromatic layer may be optionally placed under or over the mattress or between the cover and mattress. This layer can be tuned to heat up to a certain temperature where it can maintain that temperature for a predetermined period of time to disinfect the mattress and/or cover.

DETAILED DESCRIPTION OF THE INVENTION

Figure 1A:
FIG. 1A shows a perspective view of a cushioning support assembly having a foam layer and a multi-layered support enclosed within a covering.

Researchers have demonstrated that light in different wavelengths can be used to heal wounds. Most studies have used blue or red light. Blue light gets absorbed close to the surface and is known to kill bacteria directly which could be the mechanism of action. Red light penetrates deeper and could just be providing heat and improving circulation. Both of these wavelengths can now be easily produced with LED's and even lasers if needed.

The therapy can be delivered as pulsating or continuous for a limited time duration depending upon the ulcer or wound to be treated.

The light can be delivered directly to the surface of the wound by using flexible fiber optics or lasers or LEDs. The patient can be lying on a low pressure cushioning support system if the wound to be healed is the sacral pressure ulcer and light can be piped to the surface of the device or a 'light delivery flexible cover can be placed over the device to deliver the light. An alternative can be piping the light into the fluid inside of the cushioning and making the top surface of the cushioning support clear for allowing light to reach the region of the wound. This can be done by flooding the fluid region of the cushioning support with light and having the controller outside.

Generally, in a healthy individual, the presence of muscle mass and soft tissue usually functions to distribute and relieve pressure from bony protuberances of the body contacted against the underlying surface. However, when a patient is forced to lie on one portion of their body for extended periods of time, areas such as the sacrum or trochanter (or other portions of the body such as the heel, elbow, head, etc.) may compress a region of the skin and tissue between the protuberance and a contact region formed against the underlying surface.

A disinfecting light source can be integrated in a number of different configurations with a support assembly that may be worn or used to support an individual who may be immobilized, e.g., such as sitting in a wheelchair, for extended periods of time to prevent the formation of pressure ulcers. Such a support assembly may be placed against and/or beneath particular regions of the body where pressure ulcers tend to form, e.g., sacrum, trochanter, ischium, head, elbow, heel, as well as any other region of the body where support is desired. Various features which may be incorporated or included into the support assemblies described herein may be seen in further detail in the following U.S. patent application Ser. No. 13/189,320 filed Jul. 22, 2011 (U.S. Pub. 2013/0019873); Ser. No. 13/407,628 filed Feb. 28, 2012 (U.S. Pub. 2013/0019881); Ser. No. 13/683,198 filed Nov. 21, 2012 (U.S. Pub. 2013/0112213); Ser. No. 13/693,691 filed Dec. 4, 2012 (U.S. Pub. 2013/0092175); Ser. No. 13/760,482 filed Feb. 6, 2013 (U.S. Pub. 2013/0180530); Ser. No. 13/784,035 filed Mar. 4, 2013 (U.S. Pub. 2013/0180531); Ser. No. 13/784,133 filed Mar. 4, 2013 (U.S. Pub. 2013/0174855); Ser. No. 13/784,215 filed Mar. 4, 2013 (U.S. Pub. 2013/0174856); Ser. No. 13/784,260 filed Mar. 4, 2013 (U.S. Pub. 2013/0174859); Ser. No. 13/945,684 filed Jul. 18, 2013 (U.S. Pub. 2013/0298918); Ser. No. 13/065,877 filed Mar. 30, 2011 (U.S. Pub. 2011/0239372); Ser. No. 13/973,840 filed Aug. 22, 2013; and Ser. No. 14/191,212 filed Feb. 26, 2014. Each of which is incorporated herein by reference in its entirety and for any purpose herein.

Figure 1B:
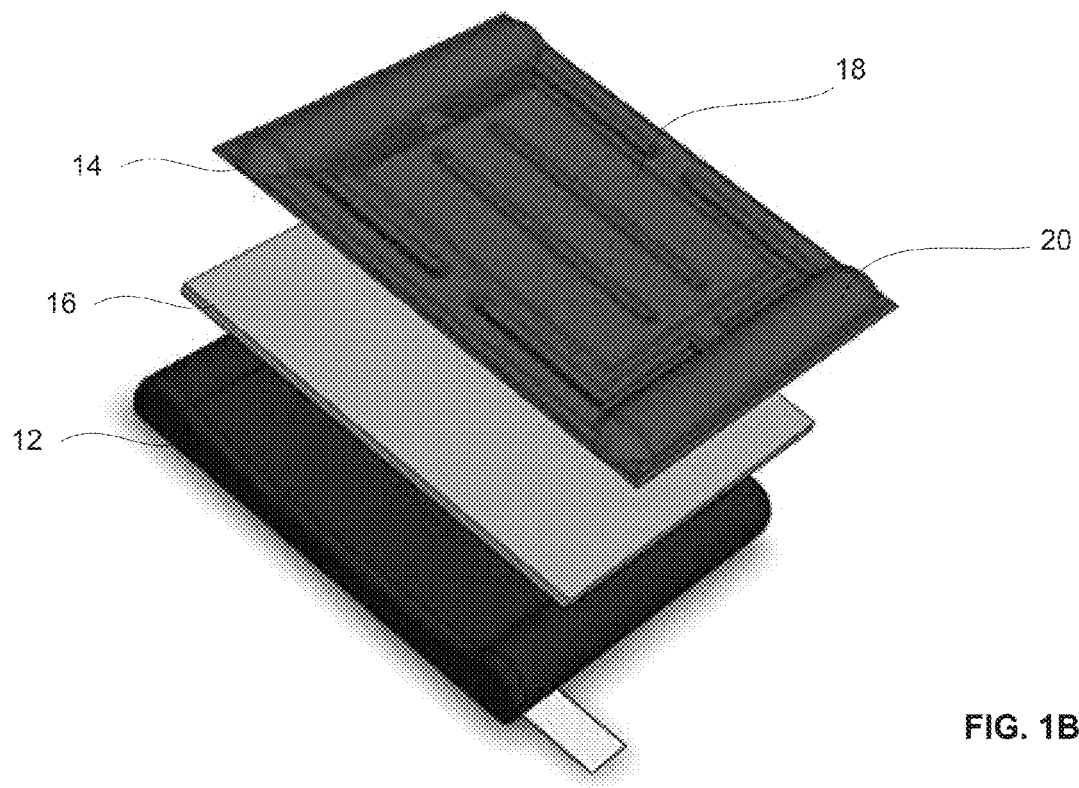
FIG. 1B shows an exploded assembly view of the individual foam layer and multi-layered support where the foam layer is positioned along the bottom surface of the multi-layered support or along the surface of the multi-layered support opposite to the contact surface.

One example of a supporting cushion is shown in the perspective view of FIG. 1A, which illustrates a cushion support 10 having a multi-layered cushioning support 14 contained within an enveloping cover 12. FIG. 1B shows an exploded assembly view of the multi-layered cushioning support 14 (described in further detail below) which may generally comprise several interconnected chambers configured to have a central support region and a surrounding support region 20 which are in fluid communication with one another. The multi-layered support 14 may be optionally filled with a gas (such as air) or liquid (such as water or mineral oil) or a combination of both. The multi-layered support 14 may also be sized in various dimensions suitable for placement under a patient body, e.g., 18 in.×20 in. for use as a cushion such as on a wheelchair. The multi-layered support 14 may also incorporate a relatively smaller secondary chamber 18 formed by an additional layer attached (such as by welding) upon the surface of the central support region 20 such that the region 20 surrounds this secondary chamber 18. The secondary chamber 18 may be filled by a volume of liquid, such as mineral oil, which is relatively more viscous than the gas or liquid filled within the central support region or surrounding support region 20. Moreover, this secondary chamber 18 may remain fluidly disconnected from the central support region and the surrounding support region 20.

Aside from the multi-layered support 14, an additional cushioning foam layer 16 may be positioned adjacent to the support 14 provided that this cushioning foam layer 16 is positioned along a bottom surface of the support 14, i.e., along a surface of the support 14 opposite from the secondary chamber 18. This is to allow for the multi-layered support 14 and secondary chamber 18 to come into direct contact against the patient's body without any other materials interfering (aside from the cover 12). The cushioning foam layer 16 may be comprised of, e.g., different density polyurethane foams, which can be fabricated into different sizes and thicknesses (e.g., 17 in.×19 in.×0.5 in.) depending upon the desired application. The foam layer 16 can be alternatively replaced by other cushioning designs such as a gel-type material, biasing springs, etc.

The cover 12 may envelope both the multi-layer support 14 and the foam layer 16 and may also be fabricated from various materials which can be breathable and waterproof. The surface of the cover 12 may also be made to have, e.g., an anti-skid surface, over its entire surface or along selective surfaces such as the bottom surface in contact with a platform. The cover 12 may be sized (e.g., 18 in.×20 in.×1.5 in.) similarly to the multi-layer support 14 and foam layer 16 which may both be inserted into the cover 12 through an opening defined along one of the edges of the cover 12. Additionally, while the individual layers 14, 16 may be maintained in their relative positioning by various mechanisms such as straps, fasteners, adhesives, etc., their relative positioning may also be maintained by the cover 12. Also, while the cover 12 may be placed atop the secondary chamber 18 for direct contact against the patient's body, the cover 12 is sufficiently thin enough so as not to interfere with the cushioning support provided the layers 14, 16.

As previously discussed, the cushioning foam layer 16 is positioned along a bottom surface of the support 14, i.e., along a surface of the support 14 opposite from the secondary chamber 18, as shown in FIG. 1B, so that the secondary chamber 18 and multi-layer support 14 may be positioned into direct contact through the cover 12, if present, against the patient's body. Having the secondary chamber 18 of the support 14 placed into contact against the patient's body allows for effective pressure distribution throughout the support 14 while the foam 16 positioned beneath the support 14 (i.e., along the surface of the support 14 opposite of the secondary chamber 18 and away from the patient's body) provides for further cushioning support of the patient's body.

Figure 2A:
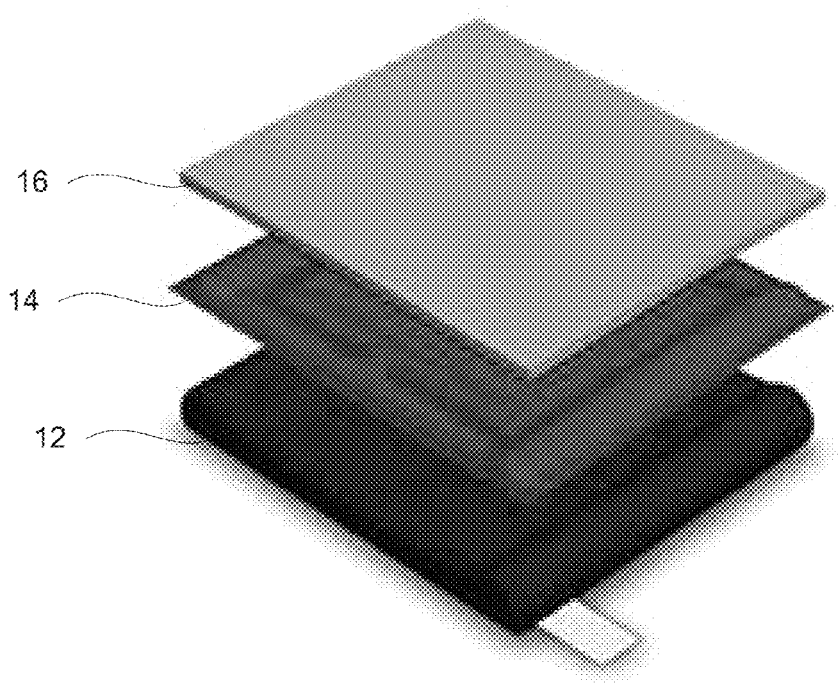
FIG. 2A shows an exploded assembly view of another variation where the foam layer is positioned upon the top surface or contact surface of the multi-layered support.
Figure 2B:
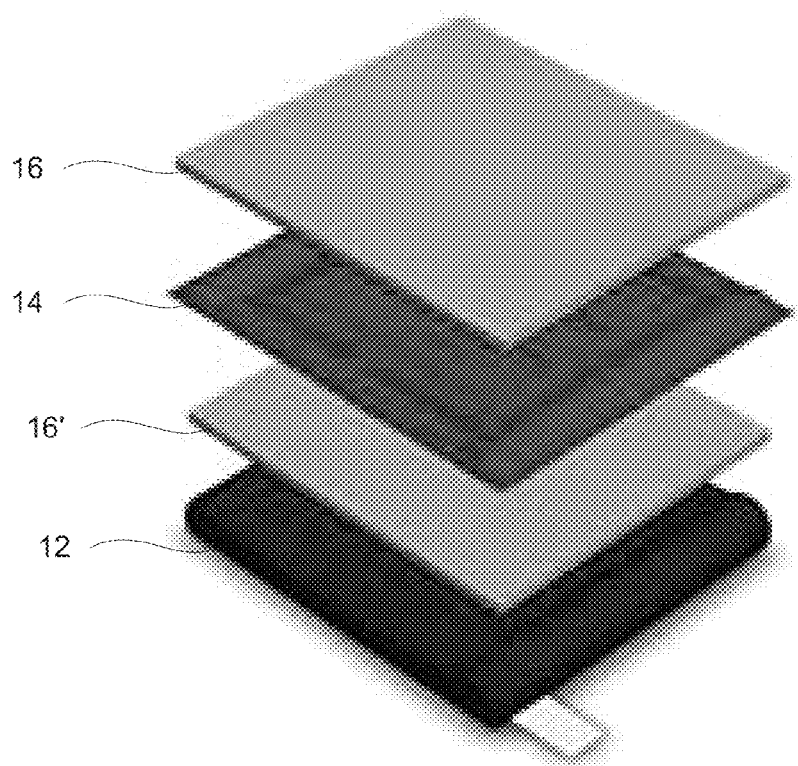
FIG. 2B shows an exploded assembly view of yet another variation where a first foam layer is positioned upon the top surface or contact surface as well as the bottom surface of the multi-layered support.

However, other variations of the cushioning support may include one example where the foam layer 16 may be positioned atop the multi-layer support 14, as shown in the exploded assembly view of FIG. 2A. In this variation, the foam layer 16 may be positioned along the same surface of the secondary chamber 18 such that the foam layer 16 comes into contact through the cover 12 with the patient's body. Another variation is shown in the exploded assembly view of FIG. 2B which is similar to the variation of FIG. 2A but with the addition of a second foam layer 16' positioned beneath the multi-layer support 14. In this case, the foam layer 16 and second foam layer 16' may be fabricated from the same or different materials and may be configured into the same or different dimensions depending upon the desired results.

Figure 3A:
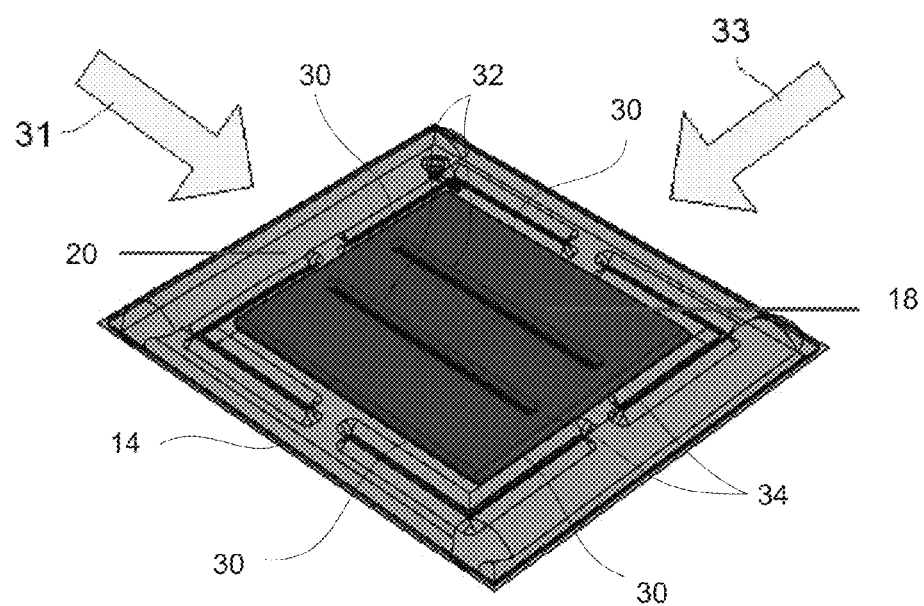
FIG. 3A shows a perspective view of the multi-layered support incorporating one or more light sources.
Figure 3B:
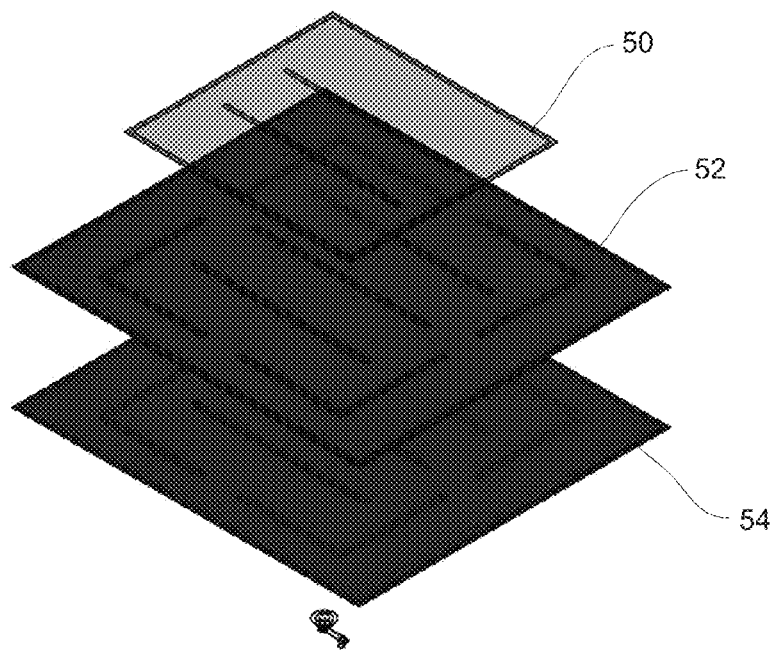
FIG. 3B shows an exploded assembly view of the individual layers forming the multi-layered support.

Turning now to the multi-layer support 14, a perspective view of one variation of the support is shown in FIG. 3A and an exploded assembly view of the individual layers forming the multi-layered support 14 is shown FIG. 3B. The secondary chamber 18 may be formed atop the support 14 via attachment along its edges 30 which may be welded, adhered, or otherwise attached. While the secondary chamber 18 may form a single chamber, one or more barriers or boundaries 32 may be formed along the secondary chamber 18 at least partially dividing the secondary chamber 18 into one or more sub-chambers which are fluidly connected to one another. The inclusion of the barriers or boundaries 32 may effectively slow or inhibit the flow of any fluids contained within the secondary chamber 18 from shifting to quickly such as when the patient adjusts their body position upon the support 14. The example shown in FIG. 3A illustrates a variation where the two barriers or boundaries 32 are formed in parallel along the secondary chamber 18 although in other variations, fewer than or more than two barriers or boundaries 32 may be formed in parallel configurations or various other configurations.

Moreover, the secondary chamber 18 may be formed to have an overall volume of, e.g., 0.6 liters, although this volume may be decreased or increased depending upon the desired results and the type of liquid contained within the chamber 18. This volume held within the secondary chamber 18 is less than the volume in the underlying support 14. This variation may contain, e.g., 0.6 liters of mineral oil, as the oil may help in reducing the pressure in combination with an underlying air layer contained within the remaining chamber of the support 14. When in use, the oil layer within the chamber 18 may be cradled by the underlying air chamber to prevent any potential "edge effects" associated with fluid interfaces. Moreover, the inclusion of the oil layer within the chamber 18 may also facilitate the delivery of cooling or heating therapy against the patient body as oil may be cooled or heated by any number of passive or active methods. Additionally and/or alternatively, the air within the remaining chamber may also be cooled or heated by any number of methods as well. However, because oil has a relatively higher specific heat than air, the oil layer within the chamber 18 may retain heat for longer periods of time.

With this multi-layer support 14, one or more light sources 31, 33 may be integrated or incorporated to transmit light through the support 14 (in particular through the fluid contained within the support) for illumination upon the patient body in contact with the support 14 to facilitate disinfection of the wound or ulcer or upon a covering to disinfect the covering. The light sources 31, 33 may transmit the light through any number of mechanisms (as described below with respect to FIGS. 5 to 8) such as optical fibers integrated within the support 14 or through a separate layer in transmissive communication with the light sources 31, 33. Moreover, the support 14 may also incorporate one or more heating elements to increase the temperature of the support 14 as well, as also described below in further detail.

As shown in the exploded assembly view of FIG. 3B, each of the individual layers forming the multi-layered support 14 may be seen. A first layer 50 forming the top layer of the secondary chamber 18 may be formed as a sheet having a thickness (e.g., 0.020 in.) made from various polymeric materials, e.g., polyvinyl chloride (PVC). The first layer 50 may be formed to have various dimensions (e.g., 13 in.×12 in.) which are shorter than the second layer 52 upon which the first layer 50 may be attached. The second layer 50 and third layer 54 may also be formed as sheets having a thickness (e.g., 0.010 in.) similarly made from various polymeric materials such as PVC. Each of the layers 52, 54 may be similarly sized to have various dimensions (e.g., 20 in.×18 in.) and may be attached to one another along seams formed around the periphery of the layers 52, 54 as well as along various locations between the sheets. However, while the second and third layers 52, 54 are attached to one another, the first layer 50 may remain attached only to the underlying second layer 52.

Figures 4A, 4B:
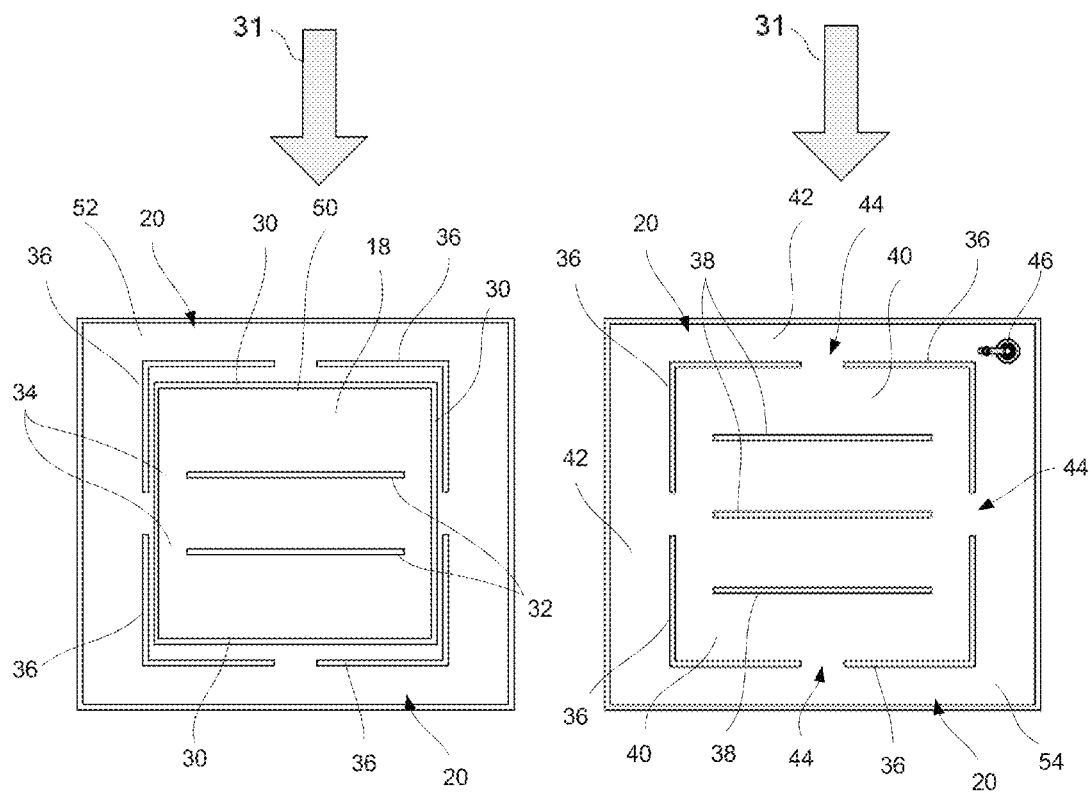
FIGS. 4A and 4B show top and bottom views, respectively, of the multi-layered support having one or more light sources.

The top and bottom views of the multi-layer support 14 are shown in further detail in respective FIGS. 4A and 4B. As illustrated in FIG. 4A, while the first layer 50 may be welded or otherwise attached to the second layer 52 around the periphery of the first layer 50 along attachment 30, the formation of the barriers or boundaries 32 may also be seen formed between the first layer 50 and second layer 52. As previously described, the barriers or boundaries 32 may be formed at least partially between the respective layers 50, 52 such that fluid passageways 34 are formed between each of the sub-chambers to allow for the passage of fluid throughout the secondary chamber 18. The fluid passageways 34 may be formed to have a width of, e.g., 1.5 in. or more.

As illustrated in the bottom view of FIG. 4B, further details may be seen between the second layer 52 and third layer 54. The second and third layers 52, 54 may be attached or otherwise welded to one another to divide the support into sub-chambers which remain in fluid communication with one another. In this variation, a central chamber 40 may be defined along a central portion of the support 14 while a peripheral chamber 42 may be formed to surround the central chamber 40. One or more barriers or boundaries 36 may be formed between the central chamber 40 and the surrounding chamber 42 by welding or otherwise attaching portions of the second and third layers 52, 54 to one another.

The barrier or boundary 36 may be formed to follow the outer periphery of the support 14 (e.g., having a width ranging from 2 in. to 3 in.) while also defining one or more fluid passageways 44 (e.g., having a width of 2 in. or more) between the central chamber 40 and the surrounding chamber 42. The fluid passageways 44 may be formed along each of the sides of the barrier or boundary 36 to allow for the passage of air between the central chamber 40 and surrounding chamber 42.

Also shown are exemplary light source 31 although any number of additional light sources as well as heating elements may be incorporated into the design of the support 14.

With the multiple layers of support as well as the use of multiple sub-chambers, the gas or liquid within the support 14 may become displaced (within each of the layers) when a portion of the patient's body is positioned thereupon. At least some of the air in the central chamber 40 may displace through one or more of the fluid passageways 44 into the peripheral chamber 42 to one or more regions adjacent to the portion of the body and cause the sides of the support 14 (e.g., the surrounding peripheral chamber 42 and any portions of the central chamber 40 adjacent to the body portion) to lift up slightly relative to the portion of the support 14 which is in contact with the body portion. Some of the oil or liquid within the secondary chamber 18 may also displace away from the body portion through fluid passageways 34 but remains within the secondary chamber 18.

As the peripheral chamber 42 lifts relative to the portion of the support 14 which is in contact with the body portion, the displaced liquid or gas may also increase the surface area of the support 14 contacting against and supporting the portion of the body resulting in a cradling effect on the body portion. For example, if the patient's hip were placed upon the support 14, the displaced air within the central chamber 40 (and/or the oil in the secondary chamber 18) may become displaced immediately below the contacted hip. The displaced liquid or gas from the central chamber 40 may flow into the adjacent peripheral chamber 42 which may rise slightly relative to the central chamber 40 such that the hip becomes cradled by the support 14. Additionally, the overall surface area of the support 14 contacting against the hip may increase and the support 14 may lift up not only the hip but the regions of the patient's body adjacent to the hip.

The central chamber 40 may also have one or more barriers or boundaries 38 defined along the central chamber 40 as well. Although three boundaries 38 are shown in parallel with one another, fewer than or greater than three boundaries 38 may be formed. Each of the barriers or boundaries 36, 38 as well as the passageways 44 may allow for fluid communication throughout the central chamber 40 and surrounding chamber 42 in a controlled manner. Additionally, the third layer 54 may also incorporate a valve 46 to allow for the passage of air into the support 14. The volume of the secondary chamber 18 may remain fluidly disconnected from the remainder of the support 14 since the secondary chamber 18 may be filled with a volume of mineral oil, e.g., 0.6 liters.

As mentioned above, the low pressure cushioning support system utilized with the light includes any of the cushioning supports or systems which are specifically designed to redistribute the supporting pressure against a patient's body. Moreover, it is intended that the delivery of lights and light therapy can be utilized in any number of combinations over any region or regions of the support.

Aside from cushioning supports, disinfection of hospital mattresses using light has also been accomplished. Bacteria and other pathogens are typically found below the cover of the hospital mattress and can lead to hospital acquired infections. To prevent this, a mattress or cushion design can include one or more sources of light which can kill bacteria and disinfect the mattress. These sources can be piped inside of the mattress under the cover or upon the exterior of the mattress and/or cover and can be turned on after every patient use to kill any bacteria and disinfect any mattress.

Bacteria die when subjected to elevated temperatures. This can be modeled based on a classical Arreneous equation. The Table 1 below shows the D-value to temperature correlation for different bacteria. D-value refers to the time required to kill 90% of the bacteria at a given temperature.

TABLE 1

D-value to temperature correlation.

| Serotype | Meat | D-value (minutes) | Temperature (° C.) |
|---|---|---|---|
| Salmonella | Chicken | 0.176 | 70 |
| Salmonella | Chicken | 0.286 | 67.5 |
| S. Typhimurium | Ground Beef | 0.36 | 63 |
| Salmonella | Ground Beef | 0.7 | 62.76 |
| S. Thompson | Minced Beef | 0.46 | 60 |
| Salmonella | Ground Beef | 4.2 | 57.2 |
| S. Typhimurium | Ground Beef | 2.13 | 57 |
| S. Typhimurium | Ground Beef | 2.67 | 57 |
| S. Typhimurium | Skin macerate[1] | 61.72 | 52 |
| Salmonella | Ground Beef | 62 | 51.6 |

Table 1 is for food but can be used to model for the disinfection of germs found on mattresses and/or covers. For example, a heating element or thermal blanket (as described in further detail below) can be operated to achieve temperatures on the mattress surface or underneath the top layer of a cover to around, e.g., 50° C. to 75° C. If the temperature is at, e.g., 50° C., the heating source can be focused on one region for about, e.g., 60-70 minutes, while decreasing to less than, e.g., 1 minute per region, if the treatment temperature rises to 75° C. The time/temperature setting of the heat source can be modeled depending on the material properties of the cover and/or mattress to prevent any adverse effect on the materials of the mattress and/or cover and also the time available between patients for disinfection.

A specialized hospital mattress typically has a cover made out of a breathable and waterproof layer. This mattress and cover can withstand temperatures typically from 57° C. and up to about, e.g., 60° C., with no damage. The light source can be set to heat up to about, e.g., 57° C., for 3 minutes in a particular location. The light source can then be moved to an adjacent area and the treatment cycle can be repeated. Once the light source scans the entire mattress and/or cover, the device be stopped and the mattress may be ready for use by another patient.

Figure 5:
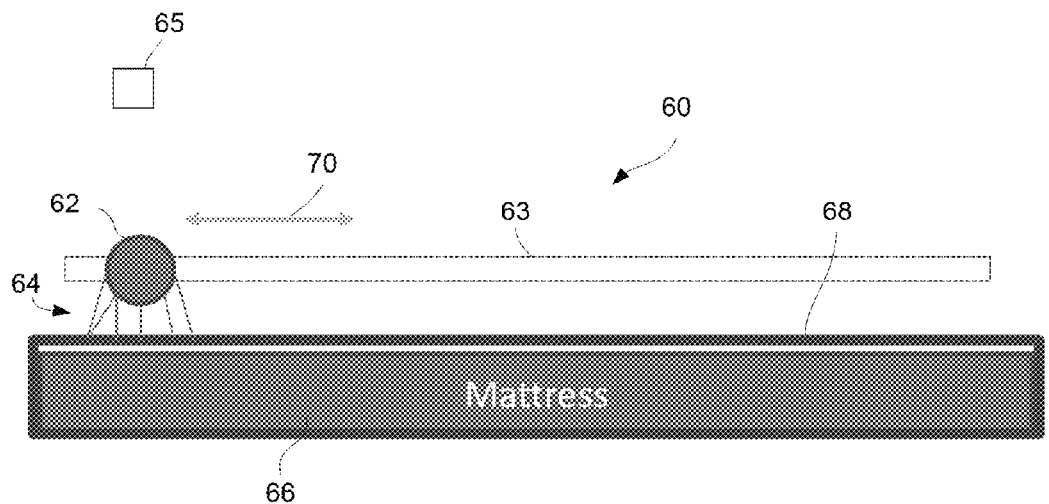
FIG. 5 illustrates a schematic partial cross-sectional side view of one variation of a mattress incorporating a disinfecting lighting system translatable over a surface of the mattress or cover.

In one variation, a light and/or heat source may be positioned over a mattress and/or cover to disinfect the mattress and/or cover as shown in the schematic partial cross-sectional side view of FIG. 5. In this variation 60, an assembly having a source of light 62 may be placed over a mattress 66 with the cover or sheet 68 in place when a person is off the bed. The light source 62 may be configured to emit light rays 64 with any number of combinations of different wavelength and/or colors (e.g., blue, red, etc.) which can be tuned to kill different kinds of bacteria and can penetrate the underlying cover 68 and mattress 66 depending on the wavelengths emitted. The light wavelengths may range anywhere from, e.g., 200 nm to 3000 nm, to provide sufficient disinfection. In addition an optional heating element or a light based heating system can be incorporated or integrated into the assembly 62 to increase the temperature below the cover 68 to temperatures which can kill any or all of the germs which may be present. Such heating elements may increase the temperature to the range and for the times described above.

This over the mattress system can be configured to include an actuator such as a roller with the assembly 62 which rolls over the cover 68 and/or mattress 66 at a fixed rate and duration staying at one place for a fixed duration, as described above depending upon the temperature applied. The roller can incorporate an actuator or motor to move the light source 62 and an optional controller 65 which may be programmed to traverse the light source 62 at a programmed rate and duration. The controller 65 may be in wired or wireless communication with the assembly 62. Alternatively, the light source 62 can be configured as a rail mounted system which scans the cover 68 and/or mattress 66 at a fixed rate while traversing over an optional rail 63 which may be mounted permanently or temporarily upon or in proximity to the mattress 66 or cover 68. In yet another alternative, the light source 62 may traverse over the cover 68 and/or mattress 66 at along an arbitrary path.

Figure 6:
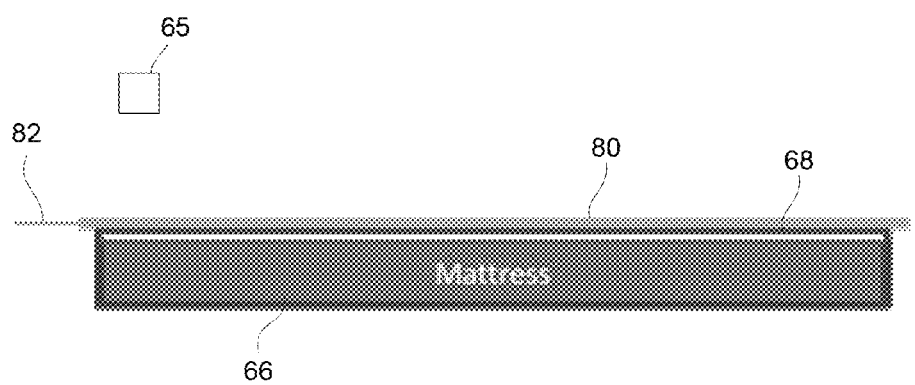
FIG. 6 illustrates a schematic partial cross-sectional side view of another variation of a mattress incorporating a blanket or covering configured to heat and/or light the underlying mattress or cover.

In another variation, the light disinfecting system can also be designed as a heating/lighting blanket or cover 80 which may be placed over the mattress 66 for disinfection, as shown in the partial cross-sectional side view of FIG. 6. The heating/lighting blanket 80 may be positioned directly upon the underlying mattress 66 or upon another cover so long as the mattress 66 is in thermal contact or communication with the heating/lighting blanket 80. The blanket 80 may then be heated to a temperature of, e.g., 57° C., and up to about, e.g., 60° C., as described above. A number of optical fibers 82 can be weaved or integrated throughout the blanket 80 in addition to resistive heating elements. To ensure good contact with the surface of the mattress 66 and/or cover 68, the blanket 80 can be anchored to the mattress 66 using, e.g., hook-and-loop fasteners, straps, hooks, weights, or any number of other fastening mechanisms. Moreover, one or more temperature sensors may be incorporated into the design of the blanket 80 for providing temperature feedback to the controller 65 for monitoring purposes.

Figure 7:
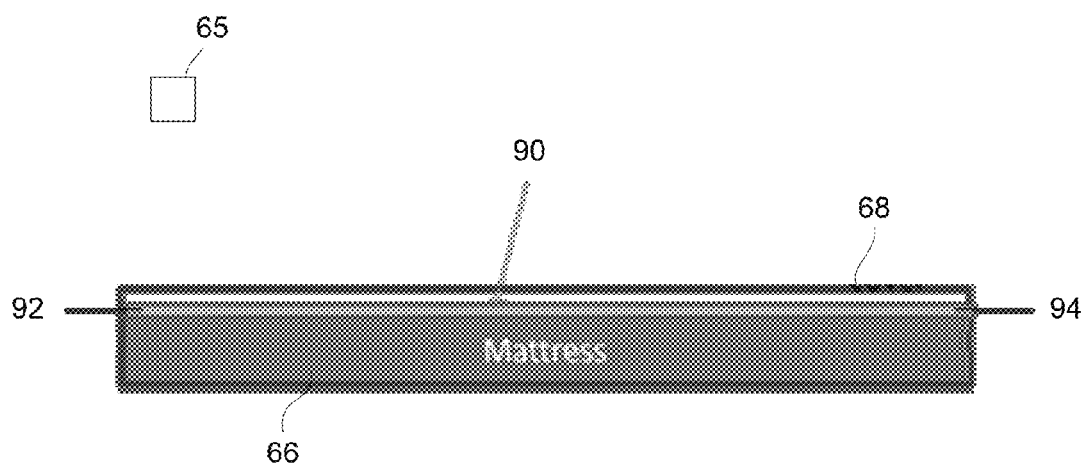
FIG. 7 illustrates a schematic partial cross-sectional side view of another variation of a mattress incorporating a fluid-filled layer configured to transmit a disinfecting light through the layer.

In yet another variation, the light disinfecting system can be integrated as a fluid-based layer 90 which may be optionally sandwiched between the cover 68 and mattress 66, as shown in the cross-sectional side view of FIG. 7. The fluid-filled layer 90 can be configured to have two light transmissive layers defining a chamber between with an overall thickness varying anywhere from, e.g., 0.5 mm to 1 cm, and can generally comprise a single chambered design over the entire layer 90 or multiple chambers which may be separated from one another such that the individual chambers remain in fluid communication with one another or are fluidly isolated from one another. The fluid contained within the layer 90 can also include any number of light transmissive fluids, e.g., oil, water, gels, or any other fluids which allow for light to pass easily through.

As the fluid contained within the layer 90 is a good conduit for the disinfecting light, the light may be piped or transmitted through the fluid from one side or multiple sides via one or more light sources 92, 94 through one or more optical fibers integrated upon the mattress 66, a secondary cover, within the fabric of the cover 68, or light sources directed to the sides of the layer 90, or any other mechanisms suitable for light transmission. Additionally, the layer 90 can also be optionally coated with a reflective surface focus the light towards the cover 68 and/or mattress 66.

In this variation and any of the variations described, the light source can be turned on or off manually or the controller 65 may be programmed to turn the light on when no one is occupying the room or bed. Moreover, the light source can be programmed to remain on for a fixed duration of time and then turn off automatically. Additionally, a pressure sensor or motion sensor can be integrated in communication with the controller 65 to turn the light source off automatically when a pressure is detected indicating that, e.g., a person or animal, is sitting upon the bed or entering the room.

Figure 8:
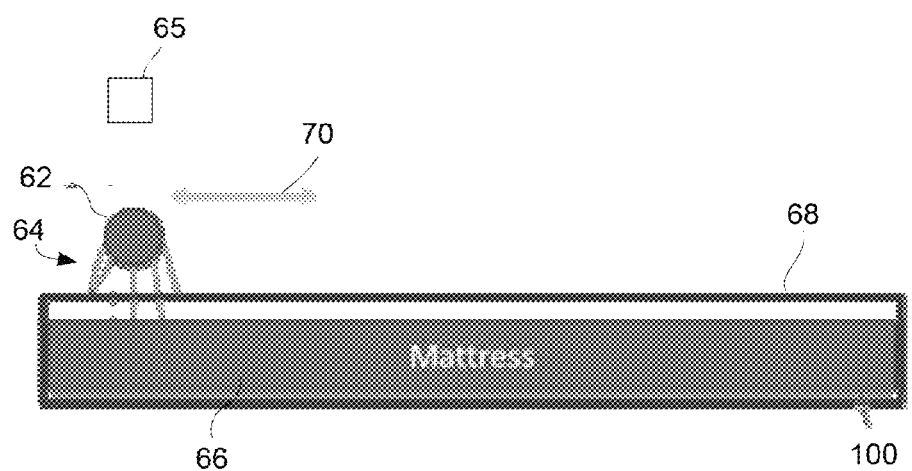
FIG. 8 illustrates a schematic partial cross-sectional side view of another variation of a mattress incorporating a thermochromatic layer.

In yet another variation shown in the partial cross-sectional side view of FIG. 8, a thermochromatic layer 100 may be optionally placed under or over the mattress 66 or between the cover 68 and mattress 66. This layer 100 can have a transition temperature in the range of, e.g., 40° C. to 100° C. The optical absorption coefficient of the layer 100 to the light is higher when the temperature is below the transition temperature. When the layer 100 heats up to the transition temperature the optical absorption coefficient to the light drops reducing the amount of absorbed light. This provides a built in control mechanism for limiting the temperature of the thermochromatic layer 100. If the light is visible, then the transition can be easily seen and may readily provide visual confirmation that the layer 100 has been heated to the transition temperature. The temperature may be maintained for a predetermined period of time to disinfect the mattress 66 and/or cover 68. The light source 62, one or more internal light sources, one or more heating elements, or any combination of light sources and/or heating elements may be used to heat the thermochromatic layer 100 to the desired temperature of, e.g., 57° C., as described above to disinfect. As the thermochromatic layer 100 heats and changes its color, it may maintain its temperature for a predetermined set duration of, e.g., 3 minutes or more.

In this and any of the variations described herein, it is expressly contemplated that any of the features can be incorporated and combined in any number of variations. For example, the light source 62 of FIG. 5 can be integrated with the blanket 80 of FIG. 6 and/or fluid-based layer 90 of FIG. 7 and/or thermochromatic layer 100 of FIG. 8 in any number of combinations, as practicable.

The applications of the devices and methods discussed above are not limited to cushions, mattresses, or covers but may include any number of further applications. Modification of the above-described device and methods for carrying out the invention, and variations of aspects of the invention that are obvious to those of skill in the art are intended to be within the scope of the claims.

What is claimed is:

1. A method for disinfecting a surface, comprising:
    illuminating a light upon a first region of a mattress or cover, wherein the light is tuned to emit one or more wavelengths suitable for disinfecting one or more bacterial strains present upon the mattress or cover;
    moving the light to at least a second region of the mattress or cover after a predetermined period of time while under control of a controller; and
    heating a thermochromatic layer in proximity to the mattress or cover.

2. The method of claim 1 wherein the illuminating comprises emitting the one or more wavelengths ranging from 200 nm to 3000 nm.

3. The method of claim 1 further comprising applying heat to the mattress or cover under control of the controller.

4. The method of claim 1 wherein the illuminating further comprises heating the mattress or cover to a temperature of up to 60° C.

5. The method of claim 1 wherein the illuminating comprises transmitting the light via one or more optical fibers.

6. The method of claim 1 wherein the moving the light comprises moving the light via a roller mechanism positioned upon the mattress or cover.

7. The method of claim 1 wherein the moving the light comprises moving the light via a rail positioned in proximity to the mattress or cover.

8. The method of claim 1 wherein the moving the light comprises moving the light along an arbitrary path over the mattress or cover.

9. The method of claim 1 further comprising positioning a fluid layer upon the mattress or cover.

10. The method of claim 9 further comprising transmitting a second light through the fluid layer.

11. The method of claim 9 further comprising anchoring the fluid layer upon the mattress or cover.

12. A method for disinfecting a surface, comprising:
    illuminating a light upon a first region of a mattress or cover, wherein the light is tuned to emit one or more wavelengths suitable for disinfecting one or more bacterial strains present upon the mattress or cover;
    moving the light to at least a second region of the mattress or cover after a predetermined period of time while under control of a controller;
    positioning a fluid layer upon the mattress or cover;
    anchoring the fluid layer upon the mattress or cover; and
    heating a thermochromatic layer in proximity to the mattress or cover.

13. The method of claim 12 wherein the illuminating comprises emitting the one or more wavelengths ranging from 200 nm to 3000 nm.

14. The method of claim 12 further comprising applying heat to the mattress or cover under control of the controller.

15. The method of claim 12 wherein the illuminating further comprises heating the mattress or cover to a temperature of up to 60° C.

16. The method of claim 12 wherein the illuminating comprises transmitting the light via one or more optical fibers.

17. The method of claim 12 wherein the moving the light comprises moving the light via a roller mechanism positioned upon the mattress or cover.

18. The method of claim 12 wherein the moving the light comprises moving the light via a rail positioned in proximity to the mattress or cover.

19. The method of claim 12 wherein the moving the light comprises moving the light along an arbitrary path over the mattress or cover.

20. The method of claim 12 further comprising transmitting a second light through the fluid layer.

\* \* \* \* \*